United States Patent [19]
Kern

[11] Patent Number: 5,362,642
[45] Date of Patent: Nov. 8, 1994

[54] METHODS AND CONTAINMENT SYSTEM FOR STORING, RECONSTITUTING, DISPENSING AND HARVESTING CELL CULTURE MEDIA

[75] Inventor: Dale G. Kern, Hyde Park, Utah

[73] Assignee: Hyclone Laboratories, Logan, Utah

[21] Appl. No.: 15,804

[22] Filed: Feb. 10, 1993

[51] Int. Cl.$^5$ ............................................. C12M 1/24
[52] U.S. Cl. .................................. 435/240.1; 222/94; 435/284; 435/296; 435/810
[58] Field of Search .............. 435/284, 296, 311, 810, 435/240.1, 240.2; 141/244; 222/94

[56] References Cited

U.S. PATENT DOCUMENTS

| | | | |
|---|---|---|---|
| 4,484,920 | 11/1984 | Kaufman et al. | 604/416 |
| 4,738,782 | 4/1988 | Yamauchi et al. | 210/650 |
| 4,829,002 | 5/1989 | Pattillo et al. | 435/284 |
| 4,902,287 | 2/1990 | Carmen et al. | 604/416 |
| 4,910,147 | 3/1990 | Bacehowski et al. | 435/296 |
| 4,912,058 | 3/1990 | Mussi et al. | 435/285 |
| 4,939,151 | 7/1990 | Bacehowski et al. | 435/284 |
| 4,968,624 | 11/1990 | Bacehowski et al. | 435/287 |
| 5,010,013 | 4/1991 | Serkes et al. | 435/285 |
| 5,069,370 | 12/1991 | Cady et al. | 464/222 |
| 5,083,686 | 1/1992 | Cady et al. | 464/222 |
| 5,225,346 | 7/1993 | Matsumiya et al. | 435/284 |

*Primary Examiner*—Robert J. Warden
*Assistant Examiner*—Krisanne M. Thornton
*Attorney, Agent, or Firm*—Workman, Nydegger & Jensen

[57] ABSTRACT

A cell culture media containment system is provided having a mixing bag substantially enclosed within a storage bag. Powdered cell culture media and other constituents are introduced into the mixing bag and are mixed therein. Thereafter, the reconstituted media is conveyed from the mixing bag into the storage bag undergoing sterilization during conveyance therebetween. The reconstituted cell culture media may then be stored in a sterilized condition in the storage bag or maybe dispensed into a cell growth container. In another embodiment of the present invention a plurality of storage bags or mixing bags may be utilized so that reconstituted cell culture media may be both mixed and dispensed while protein-laden cell culture media may be simultaneously harvested back into another of the plurality of storage bags.

19 Claims, 6 Drawing Sheets

METHODS AND CONTAINMENT SYSTEM FOR STORING, RECONSTITUTING, DISPENSING AND HARVESTING CELL CULTURE MEDIA

BACKGROUND

1. Field of the Invention

The present invention relates to methods and apparatus for storing, reconstituting, dispensing and harvesting cell culture media for use in growing cells. More specifically, the present invention is a cell culture media containment system designed to allow users to reconstitute powdered cell culture media and then store the reconstituted media in a sterile condition until desired for use. The reconstructed cell culture media may then be dispensed from, and harvested into, the containment system.

2. Background Art

Cell culture media is typically a solution of amino acids, electrolytes, serum, serum fractions, vitamins, and growth factors. The constituents of cell culture media are combined in quantities to adjust the pH, osmolarity and other essential parameters for consistent, rapid cell growth therein.

Cell culture media provides an environment in which cells may exist and either develop within themselves a desired protein during growth or secrete the desired protein or other cellular product into the surrounding medium as a by-product of growth. Those cells that develop the desired protein within their structures must be chemically or mechanically fragmented in order to harvest the desired protein. More complex cells such as mammalian cells can produce sugar-modified cellular products and secrete the desired glycoprotein products into the cell culture medium for easy collection.

Cell culture medium is typically sold in either a liquid or a powdered form. The advantages to the liquid form are that sterile liquid cell culture media may be immediately introduced into the container in which the cells will grow. The disadvantage to liquid media, however, is that it is less stable during shipment and storage and, therefore, requires tighter inventory control. Typically, liquid media must also be stored in a refrigerated environment, and because of its relatively high weight when compared to powdered cell culture media, shipping is more expensive. Also, the shipping bags used in conveying liquid media must be strong enough to prevent leaks from occurring.

As liquid cell culture media is typically in a sterile condition when shipped, shipping bags must be strong enough to prevent any contamination or leakage from occurring. During shipping, the stresses produced by the liquid media contained with the bags can lead to leakage and contamination. Most bags utilize a construction whereby two sheets of a plastic material are joined by thermal or chemical bonding to form a single layer pillow-shaped bag having two longitudinal seams. The open ends of the cylinder are then sealed using known techniques and access apertures are formed through the bag wall through which liquid media may be introduced into the storage bag.

During shipping, and during subsequent storage or use, the longitudinal side seams of the storage bags are exposed to pressures both from within and from without the bag. Most leakage or contamination occurs from these seams.

As a result of the increased costs and risks involved in shipping and storing liquid cell culture media, users of larger quantities of cell culture media generally purchase the media in a powdered form. This powdered form requires less storage space, is easier to ship, and remains stable over a longer period of time.

Powdered media, however, necessitates the use of equipment to reconstitute the powdered media into a liquid form prior to introduction into the cell growth container. The equipment used to reconstitute the powdered media must be thoroughly cleaned and autoclaved between uses to obtain the sterility necessary to process the media prior to introduction into the cell growth container. This sterilization equipment is expensive, bulky, and difficult to maintain in a sterile condition.

Another disadvantage of powdered media is that, due to the exacting standards required of the end product, the reconstitution of the powdered media into a liquid form requires careful and meticulous preparation to ensure that the media constituents are added in the exact amount required. Factors such as spillage, airborne drift, retention of the powdered media within the container in which it is shipped, and other environmental or handling conditions can result in reconstituted cell culture media not falling within the required parameters for consistent rapid cell growth.

Powdered cell culture media is typically reconstituted by mixing powdered cell culture media and water for injection in a rigid container. During mixing, it is not uncommon for powdered cell culture media to become airborne and distributed throughout the environment surrounding the mixing area. Spillage may also occur.

After mixing of the water for injection and powdered cell culture media, the reconstituted cell culture media is then processed through sterilization equipment using any of the known sterilization techniques.

As reconstituted cell culture media must be in a sterile condition prior to introduction into the cell growth container, the sterilization process for reconstituted cell culture media is typically conducted as the last step prior to introduction of the media into the cell growth container or into sterile storage bags. Although verification of sterility may take some time, certain applications may rely on the sterilization process used and introduce the sterilized media into the cell growth container or bioreactor.

Sterilization is particularly important in cell culture media because the media is normally used to culture specific biological substances wherein the presence of unidentified, viable, biological organisms would lead to misleading, anomalous, or invalid results. One drawback to sterilization immediately prior to introduction of the cell culture media into the cell growth container is that the sterilization equipment must be located on-site. This equipment requires storage space and represents an investment in equipment which must be borne by each individual user.

After sterilization, the sterilized media is then stored in rigid drums or stainless steel barrels.

In light of the foregoing, therefore, there exists in the art a need for methods and apparatus for the storing and reconstituting of powdered cell culture media which simplify the difficult task of properly reconstituting the powdered media into a liquid form.

A further need exists in the art for methods and apparatus for storing and reconstituting powdered cell culture media which provide the advantages of the use of a powdered cell culture media while alleviating some of the need for expensive and complicated reconstitution and sterilization equipment.

Additionally, a need exits in the art for methods and apparatus for the reconstitution of powdered cell culture media which alleviate the risk of spillage and the task of cleaning after reconstitution.

Another need in the art is for methods and apparatus for the storing and reconstitution of powdered cell culture media which reduce the risk of contamination and reduce wasted materials due to improper preparation.

A further need exists in the art for methods and apparatus for the shipping and storing of powdered cell culture media which relieve the stresses imposed on the seams of the contaminant bag during shipping.

Still further, a need exists in the art for methods and apparatus for the shipping and storing of powdered cell culture media which alleviate the high shipping cost due to the shipment of the liquid components in a cell culture media.

An additional need exists in the art for methods and apparatus for the reconstitution of cell culture media which allows the mixing and storage of cell culture media to occur in less than two separate bags requiring separate support structures.

Another need exists in the art for methods and apparatus for the dispensing and harvesting of cell culture media which allows mixing, dispensing and harvesting to occur simultaneously in a system requiring only one support structure.

OBJECTS AND BRIEF SUMMARY OF THE INVENTION

The present invention seeks to resolve problems incident to the preparation of cell culture media. More specifically, the apparatus of this invention constitutes an important advancement in the art of reconstituting powdered cell culture media.

One object of the present invention is to provide methods and apparatus for the storing and reconstitution of powdered cell culture media which simplify the difficult task of properly reconstituting the cell culture media into a liquid form.

Another object of the present invention is to provide methods and apparatus for storing and reconstituting powdered cell culture media which provide the advantages of the use of a powdered cell culture media while alleviating the need for expensive and complicated reconstitution and sterilization equipment.

An additional object of the present invention is to provide methods and apparatus for the reconstitution of powdered cell culture media which alleviate the risk of spillage and the task of cleaning up after reconstitution.

Yet another object of the present invention is to provide methods and apparatus for the storing and reconstitution of powdered cell culture media which reduce the risk of contamination and reduce wasted materials due to improper preparation.

Still another object of the present invention is to provide methods and apparatus for the shipping and storing of powdered cell culture media which relieve the stresses imposed on the seams of the bag during shipping.

A further object of the present invention is to provide methods and apparatus for the reconstitution of powdered cell culture media which reduce the high shipping costs due to the shipment of the liquid component of the cell culture media.

Yet another object of the present invention is to provide for methods and apparatus for the reconstitution of powdered cell culture media which do not require equipment that occupies valuable space in a laboratory.

Still another object of the present invention is to provide for methods and apparatus for the reconstitution of powdered cell culture media which provide a stable form of media thereby alleviating the need for stringent inventory control.

Another object of the present invention is to provide for methods and apparatus for the reconstitution of powdered cell culture media which do not necessarily have to be stored at refrigerated temperatures.

A further object of the present invention is to provide for methods and apparatus for the reconstitution of cell culture media which allows the mixing and storage of cell culture media to occur in less than two separate bags requiring separate support structures.

A still further object of the present invention is to provide methods and apparatus for the dispensing and harvesting of cell culture media which allows mixing, dispensing and harvesting to occur in a system requiring only one support structure.

Additional objects and advantages of the invention will be set forth in the description which follows or may be learned by the practice of the invention. The objects and advantages of the invention may be realized and obtained by means of the instruments and combinations particularly pointed out in the specification, drawings and appended claims.

To achieve the foregoing objects and in accordance with the invention as embodied and broadly described herein, a containment system is provided for storing, reconstituting, dispensing and harvesting powdered cell culture media. One preferred embodiment of the apparatus of the present invention comprises an outer storage bag and inner mixing bag housed within a rigid container. A mixing chamber formed within the mixing bag is capable of being placed in communication with one or more storage chambers formed in the storage bag. The mixing bag resides substantially within one or many of the storage chambers. The mixing bag is adapted to receive powdered cell culture media and other constituents therein. The powdered cell culture media is reconstituted by the introduction of both powdered and liquid constituents into the mixing chamber through an access port.

Between the mixing chamber and the storage chamber a pump may be located which acts to convey the reconstituted media from the mixing chamber to the storage chamber through a tubing system therebetween. A filter is placed in the tubing system between the pump and the storage chamber to sterilize the media passing therethrough prior to entry into the storage chamber. Thereafter, reconstituted media in the storage chamber can either be stored therein or dispensed therefrom into a cell growth container.

In one embodiment of the present invention, means for dispensing the reconstituted cell culture media are provided. The means for dispensing comprise a dispensing flange, upstanding walls and a dispensing plate having an aperture formed therethrough. The dispensing flange is affixed to the wall of the storage bag surrounding a hole formed therein. A tubing system may be attached to the dispensing plate thereby allowing the reconstituted cell culture media to flow through the aperture formed through the dispensing plate. The generation of negative or positive pressure by physical or mechanical means initiates the flow of cell culture media through the dispensing plate and attached tubing system.

After the reconstituted media is introduced into the cell growth container, and the cells have produced the desired protein, the media may then be collected and stored again for processing. The media is collected by returning the media to the storage chamber through the dispensing plate. Alternatively, a special collection port and tubing system could also be formed in the wall of the storage bag. Negative pressure applied to the tubing or positive pressure applied to the cell growth container may be used to return the media to the storage bag. Additionally, in one embodiment of the present invention, harvested media may be collected in one of a plurality of storage chambers.

The present invention also comprises a method for storing cell culture media. The method comprises the steps of introducing cell culture media into a mixing bag substantially encompassed by a storage bag and sealing the mixing bag.

The present invention also contemplates a method for reconstituting the powdered cell culture media. The steps of reconstitution encompass introducing fluid into a quantity of powdered cell culture media in the mixing chamber. One of these fluids is preferably water for injection which is a major component in reconstituting the powdered cell culture media. The water for injection is preferably introduced into the mixing chamber through an introduction plate. The introduction plate has several apertures formed therethrough, each aperture having a barbed tubing connector extending both inwardly and outwardly from the introduction plate.

In another step, the powdered cell culture media and water for injection are mixed by pumping air through the aperture in the introduction plate having a tube attached thereto depending into the mixing chamber. The tube extends downwardly near the bottom of the mixing chamber and emits the recirculated air which forms into bubbles which pass upwardly through the powdered cell culture media and the water for injection thereby mixing the ingredients in the mixing chamber.

Alternately, the powdered cell culture media could be introduced after the water for injection if the powdered cell culture media was shipped in a container separate from the mixing and storage bags.

In addition, other methods may be utilized to mix the constituents in the mixing chamber. As the media in the mixing chamber has not yet undergone sterilization, aseptic mixing techniques such as the insertion of a folding propeller into the mixing chamber may be utilized.

After the powdered cell culture media and water for injection have been combined, other ingredients are then added to adjust the specific pH, osmolarity, and other factors bringing the solution into the acceptable parameters for cell growth. Exemplary of the materials which may be added are sodium bicarbonate, serum, serum fractions, vitamins, and growth factors.

After reconstitution and adjustment, the media is then conveyed from the mixing chamber to the storage chamber. In one preferred embodiment, the mixing bag is essentially surrounded by the storage bag, but it can be understood that the mixing bag and the storage bag can be located in many configurations as long as the two are separated by one or more flexible barriers.

Media is conveyed from the mixing chamber to the storage chamber through a series of tubes, one tube depending into the mixing chamber from the introduction plate. A contiguous barbed tubing connector on the outside of the introduction plate has attached thereto a tube which then is connected to the pump. A similar section of tubing is attached to the other side of the pump and extends outwardly from the dispensing plate. Also located within this arrangement of tubing and pump is a filter to sterilize the reconstituted media prior to introduction to the storage chamber.

Although the preferred embodiment of the present invention utilizes a filter to sterilize the reconstituted media, any of the presently known methods for sterilization may be employed. When use of the reconstituted media is desired, the media may be dispensed from the storage chamber through tubing attached to the dispensing plate.

When growth of the cells has advanced to the point that sufficient cellular products have been produced, the cellular products may be harvested by removing the cell culture media from the cell growth container and conveying the media to a storage chamber. This recovered cell culture media may then be shipped in the storage bag to facilities to recover the desired cellular products.

In embodiments of the present invention employing a plurality of storage bags, reconstituted cell culture media may be introduced into a cell growth container concomitant with the collection of harvested cell culture media into another storage bag. In fact, powdered cell culture media may be reconstituted in the mixing bag while previously reconstituted media in one of the storage bags is being introduced into a cell growth container and while cell culture media is being harvested from yet another cell growth container and is being placed into one of the other storage bags.

It can be appreciated, therefore, that the inventive containment system is designed to provide the advantages of lightweight and safe shipment of powdered cell culture media and also provide the facilities to reconstitute the media on site. No expensive equipment need be sterilized for the reconstitution process as the process requires only a pump and a filter. The present invention alleviates the need for cleaning and prevents spillage by having the entire mixing process occur within the mixing bag. Once the reconstituted media has been introduced into the cell growth container, the entire containment apparatus may be discarded. The design of the inventive container allows for the reconstitution, sterile filtration, and storage of the reconstituted media to be completed in one container. To add rigidity to the system, the inventive container is often placed within a standard 55-gallon barrel or other means which add rigidity to and support the system. Other rigid support containers, such as reinforce cardboard containers may also be used. These cardboard containers may house containment systems of 1000 liters. The present invention is contemplated for use with rigid containers of many sizes from small 5 liter systems to large tanks holding thousands of gallons.

BRIEF DESCRIPTION OF THE DRAWINGS

In order that the manner in which the above-recited and other advantages and objects of the invention are made, a more particular description of the invention briefly described above will be rendered by reference to specified embodiments thereof which are illustrated in the appended drawings. Understanding that these drawings depict only typical embodiments of the invention and are, therefore, not to be considered limiting in its scope, the invention will be described with additional specificity and detail through the use of the accompanying drawings in which.

DETAILED DESCRIPTION OF THE PREFERRED EMBODIMENTS

The present invention can be best understood by reference to the claims, specification and dependent drawings, wherein like parts are designated with like numerals throughout. The present invention as it pertains to the containment system can be best understood with reference to FIG. 1.

Figure 1:
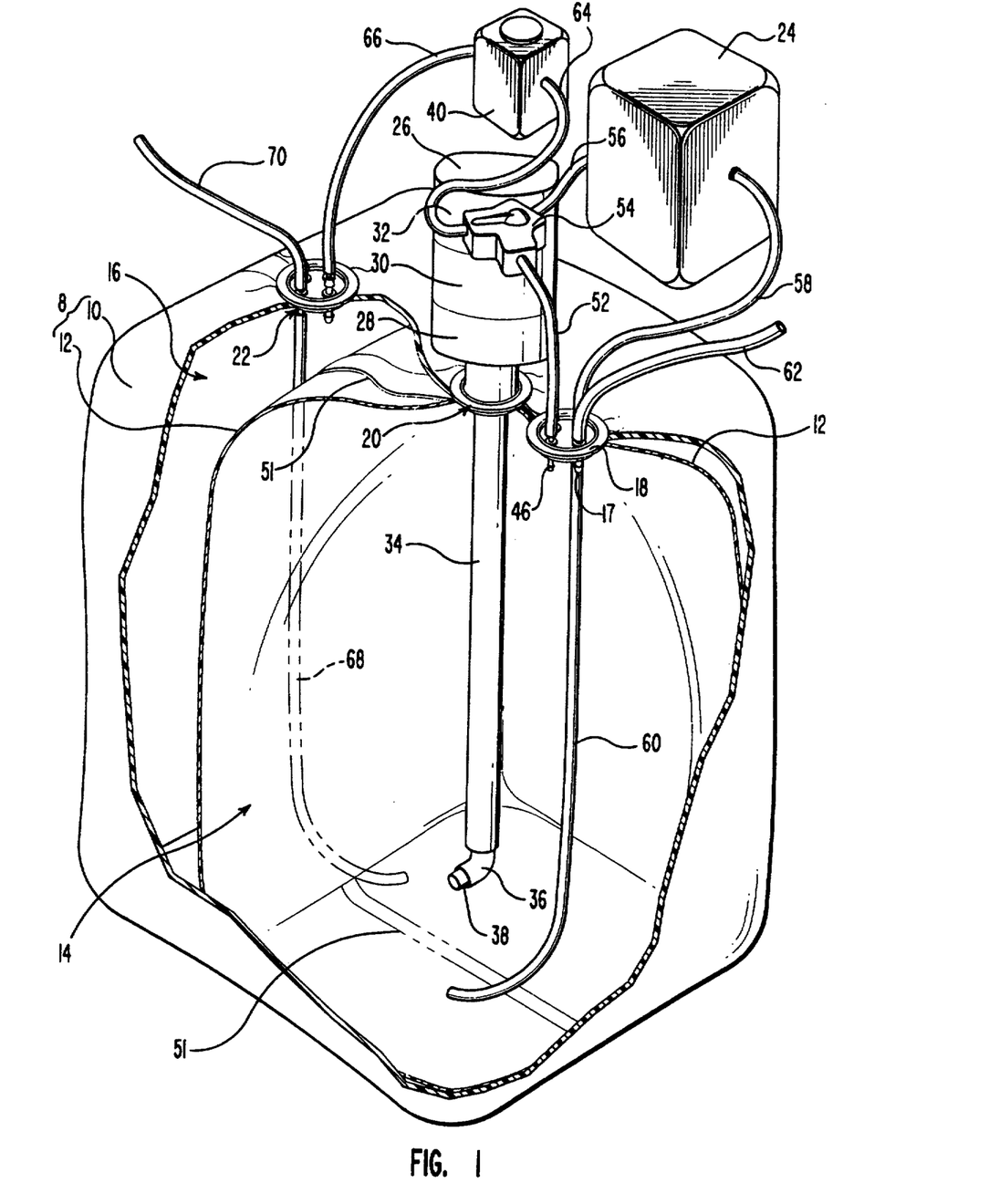
FIG. 1 is a perspective view of a preferred embodiment of the present invention with a cut-away section allowing the depiction of the mixing bag within the storage bag.

FIG. 1 is a perspective view of a containment system falling within the scope of the present invention. The containment system of the present invention is used for storing powdered cell culture media, conveying that powdered cell culture media to a site, reconstituting the powdered cell culture media into a liquid form, and dispensing cell culture media into a cell growth container.

As used in this specification, the term "reconstitute" is defined to mean the formulation of a liquid cell culture medium and does not imply that the constituents of that liquid were ever combined in a liquid form prior to the powdered form thereof.

After the cells in the cell growth container have produced sufficient protein to warrant harvesting, the cell culture media may be removed from the cell growth container and transferred back into the containment system for conveyance to a facility for processing the desired protein.

One advantage of the present invention is that the containment system may be simultaneously used to both store reconstituted cell culture media, dispense that media into a cell growth container, and withdraw media from a cell growth container for storage until processing of the protein contained therein is performed.

Containment system 8 is comprised of an outer storage bag 10 and an inner mixing bag 12. A mixing chamber 14 is formed within mixing bag 12. Likewise, a storage chamber 16 is formed within storage bag 10. Storage chamber 16 substantially envelops mixing bag 12. Although many materials can be employed for use in the construction of both a storage and mixing bags, any material chosen should preferably pass USD Class 6 cytotoxicity testing to assure that no reaction will occur with the media contained therein. The outer layer of the storage bag is preferably EVA/Nylon/EVA or its functional equivalent. Mixing bag 12 is constructed of a plastic film which is preferably made of two layers of ultra-low density polyethylene in which no slip additives or colorings have been introduced. It is important that the materials selected for the walls of both the storage bag and the mixing bag have qualities which will not compromise the sterility of the media stored therein. By constituting the bags of two-layered material, additional strength and leak resistance are imported to the containment system. Punctures or abrasions must pass through both layers to cause leaks or contamination. Although the preferred embodiment in FIG. 1 uses a two-layer material for construction of each bag wall, the present invention contemplates materials using one or many layers.

The presently preferred embodiments of the instant invention are produced in 100, 200, 400, 800, 1,000 and 1,200 liter sizes, however, the invention disclosed herein could be embodied in bags of any volumetric capacity. In addition to the concern over the reaction of the media with the materials from which the bags are constructed, a further consideration is the tolerance of the bag materials to the various forms of sterilization which may be applied to both the bag and powdered cell culture media shipped therein. Thus, materials used in the construction of storage bag 10 and mixing bag 12 should be capable of withstanding radiation, ethylene oxide exposure or other known sterilization techniques.

In addition, the materials from which storage bag 10 and mixing bag 12 are constructed must also be non-reactive with the cells and their byproducts which are harvested from the cell growth container. Media containing harvested cells will have different characteristics than the media which is reconstituted within the bag prior to introduction into the cell-growth container.

Additionally, as mixing bag 12 serves as a mixing compartment, a reconstitution compartment and an additive receptacle, the materials from which mixing bag 12 is constructed must be tolerant of the individual constituents of the reconstituted cell culture media as well as the overall cell culture media itself.

By having all constituents introduced into the mixing bag through introduction orifices 17 in introduction plate 18, the inventive system overcomes the problem of wasting constituents or of introducing those constituents into the surrounding environment. This advantage not only reduces the costs of mixing, in that less constituents are lost to the atmosphere, but also reduces the attendant cost and labor involved in cleaning up from the mixing process. All mixing of constituents for the reconstitution of powdered cell culture media used in the present invention are introduced into mixing chamber 14 prior to or during agitation. As all mixing occurs within mixing chamber 14, there is little chance of spillage or waste.

Storage bag 10 is manufactured from an extruded gusseted tube. One end of the gusseted tube has a thermal weld 51 forming a bag having one open end. Likewise, mixing bag 12 is also formed from a extruded gusseted tube and has one end thermally welded to form an open bag. Mixing bag 12 is inserted into storage bag 10 and both open ends are sealed with a common thermal weld thereby joining storage bag 10 to mixing bag 12 at thermal weld 51.

At this point, mixing bag 12 is substantially enclosed within storage bag 10 having a permanent contact between the bags only at the common thermal weld. After the manufacture of the bags, access port 20, introduction plate 18, and dispensing plate 22 are incorporated into the appropriate bags or combination of bags.

For example, dispensing plate 22 is incorporated into storage bag 10 to dispense fluids therethrough. Access port 20 and introduction plate 18, however, must pass through both storage bag 10 and mixing bag 12 to allow communication therethrough. The points where access port 20 and introduction plate 18 pass through both bags, therefore, will be points where the bags are permanently joined together.

To prevent binding and allow interaction between the two bags, access port 20 and introduction plate 18, are generally located somewhere near the common thermal weld that joins and seals the two bags. As dispensing plate 22 passes through only one bag, it can be located wherever it functions most easily.

A rigid support barrel 49 is used with this containment system to provide support to the sides of the bags when they are filled with liquid. As the only seams used in the containment system are located at the top and bottom of the bags, no significant chance of leakage is presented. The barrel in which the bags are placed provides lateral support and little pressure is exerted on the top of the bag. The bottom of the bag is also supported by the barrel. The support barrel prevents access, however, to the sides and bottom of the bag once filled with liquid. It is preferred, therefore, to have dispensing plate 22 located at the top of the bag or at a location accessible through a panel in the side of the barrel to provide easy access thereto.

To introduce constituents into the mixing bags of the present invention, a means for introducing reconstitution constituents into the mixing chamber is provided. By way of example and not limitation, the introducing means of the embodiment illustrated in FIG. 1 comprise introduction plate 18 and access port 20.

To convey reconstituted cell culture media from mixing bag 12 into storage bag 10, a series of tubes and a means for conveying are required. By way of example and not limitation, the means for conveying reconstituted cell culture media from the mixing chamber to the storage chamber provided in the embodiment illustrated in FIG. 1 comprise a peristaltic pump 24 and attendant tubing. Pump 24 as used with this embodiment is a Cole Parmer peristaltic pump with a size 18 pump head. Other pumps may be used with equal or better flow rate with compatible tubing to fit the pump head. Pumps with lower flow capacity may require longer circulation than preferred for the reconstitution process. Pumps producing higher pressure may create undue turbulence within the system.

Powdered cell culture media may be introduced into mixing bag 12 on site through access port 20. In one embodiment of present invention, powdered cell culture media and other constituents are contained within a constituent container 26. Constituent container 26 holds a predetermined amount of powdered cell culture media and other powdered constituents. Constituent container 26 may employ a plurality of compartments. Each of the compartments may contain a different constituent used in the preparation and reconstitution of the cell culture media.

For example, in the embodiment illustrated in FIG. 1, the first compartment 28 stores the powdered cell culture media. The second compartment 30 stores sodium bicarbonate which can be added to the reconstituted media to adjust the pH of the final media product. A third compartment 32 is used to store additional constituents which may comprise serum, serum fractions, growth factors, or any other constituents which may be necessary for the particular cells to be grown in the reconstituted cell culture media.

A conduit 34, spout 36 and a sleeve 38, function to assist in the introduction of the constituents into mixing chamber 14 during the reconstitution process to be discussed in detail later.

The inventive containment system is also provided with a means for sterilizing the reconstituted cell culture media as the reconstituted cell culture media is conveyed to the storage compartment. By way of example and not limitation, the means for sterilizing provided in the embodiment illustrated in FIG. 1, comprise a filter 40. Filter 40 is a sterilizing grade 0.2 micron pore size filter residing in a disposable capsule. Filter 40 is connected to the tubing at both sides over barbed tubing connectors provided with the disposable capsule. All components of filter 40 should be irradiation compatible at 2.5 mRads if this form of sterilization is employed. It will be appreciated that many methods for sterilization may be employed in the present invention, however, filtration avoids the need for expensive on-site sterilization equipment which occupies valuable laboratory space.

Figure 2:
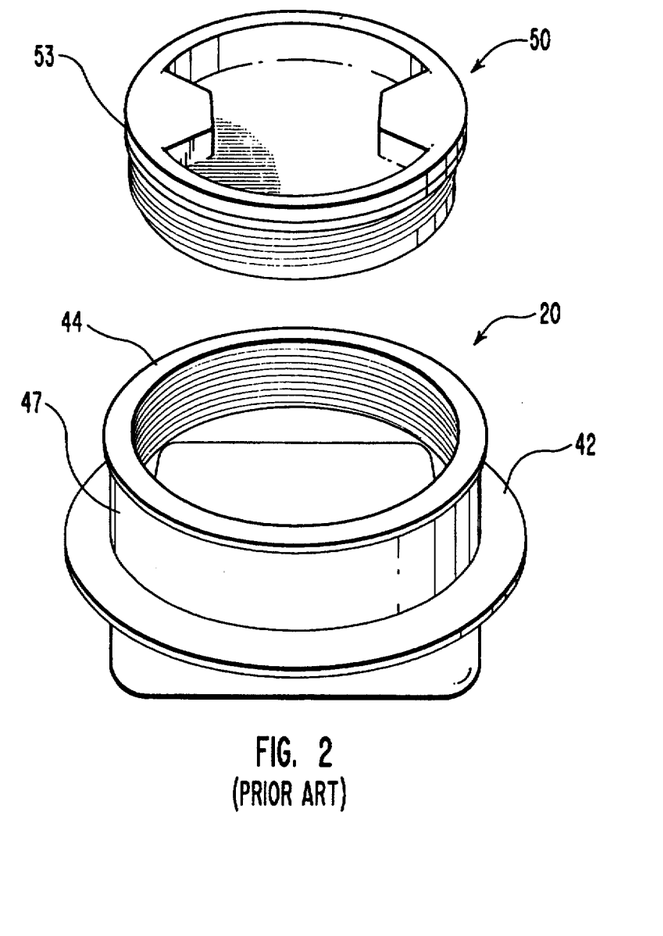
FIG. 2 is a perspective view of a prior art plate for use in introducing constituents into the mixing bag or for dispensing reconstituted media from a storage bag.

The detailed structures employed in access port 20 are best understood with reference to FIG. 2. Although introduction plate 18 and dispensing plate 22 serve disparate purposes, their construction and associated structures may be similar to access port 20. Hence, only the structures associated with access port 20 will be discussed herein with all references and discussion applying equally to dispensing plate 22 and introduction plate 18. Access port 20 is comprised of an attachment flange 42, a mounting flange 44, and an upstanding sidewall 47. The inner side of mounting flange 44 is threaded to accept a plug 50. Located under a shoulder near the top of plug 50 is a rubber washer 53.

During construction of containment system 8, a hole is formed in either storage bag 10 or through both storage bag 10 and mixing bag 12 into which the respective introduction or dispensing plates are affixed. Introduction plate 18 may be either thermally welded or chemically bonded at attachment flange 42 to the bag surrounding the hole formed therethrough.

Figure 3:
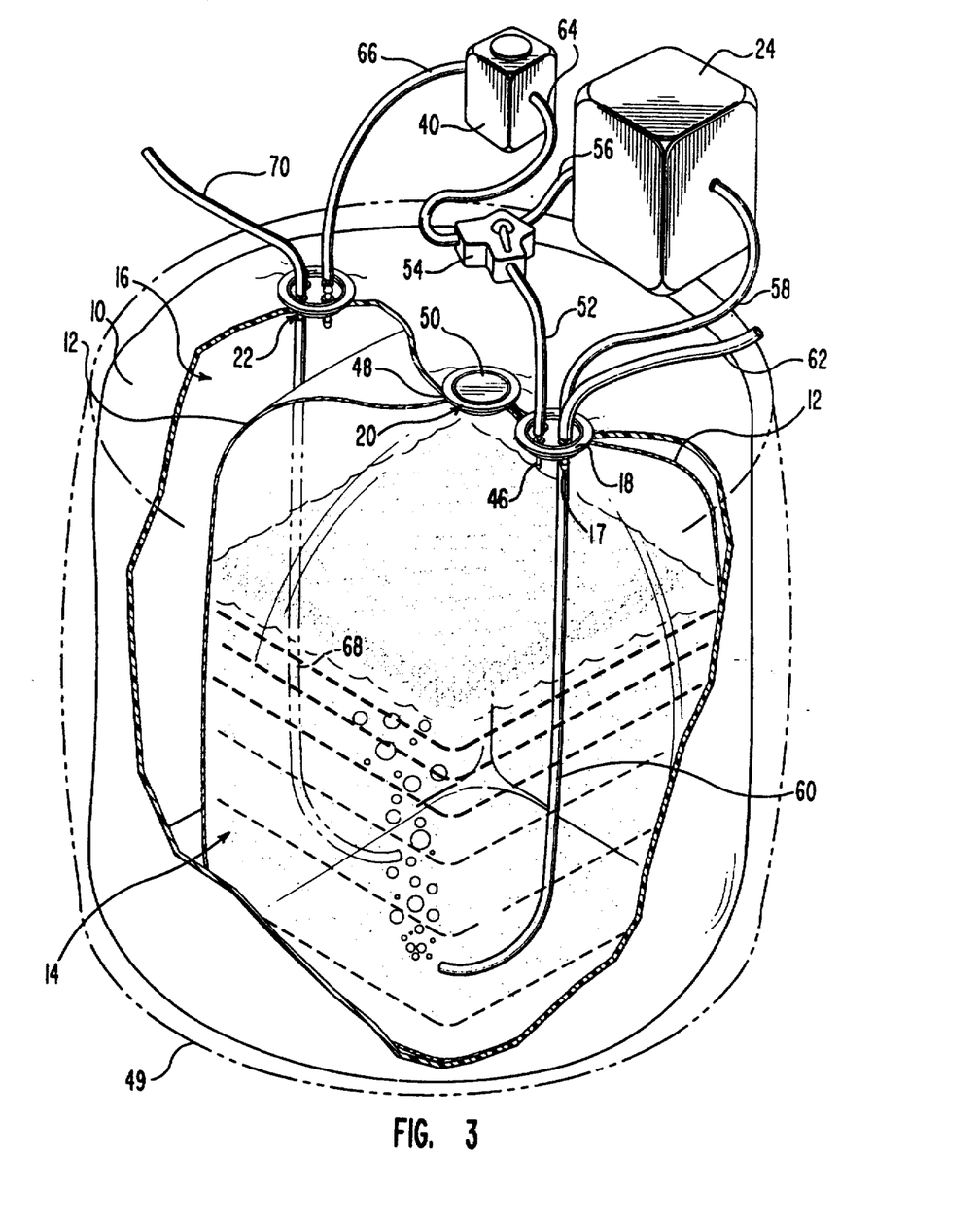
FIG. 3 is a perspective view of the preferred embodiment of the present invention depicted in FIG. 1, illustrating the reconstitution of the cell culture constituents within the mixing bag.

Referring now to FIG. 3, the structures associated with the reconstitution method will be discussed in more detail. As discussed briefly, sterilization is an important aspect in preparing media to assure proper cell growth and production of cellular products. Whereas irradiation of the container is practiced in the preferred embodiment, it should be understood that additional methods of sterilization will be known to those of skill of the art such as gas sterilization, dry-heat, and steam. Generally, in microbiological laboratories, steam is used for the sterilization for culture media, equipment and glassware; dry-heat is used for glassware and metallic equipment; gas is used for instruments; filtration is used for solution; and radiation and ethylene oxide are used for other specific purposes.

As sterilization is an evolving technology with constant improvements in equipment design and control, it is appreciated that many sterilization techniques may be applied to the instant invention. Filter sterilization, however, is preferred in the present invention to prevent destruction of heat-labile medium components.

Most simple media for cultivation of bacteria can be autoclaved prior to use, but larger volumes of media require longer autoclaving times. Vessels containing approximately 10 liters of liquid should be autoclaved at 120 degrees Celsius for 30–90 minutes depending upon media constituents. Media containing solids may require up to 90 minutes for complete sterilization of a 10 liter volume.

Complex media are likely to contain components with higher levels of temperature sensitivity. Media containing only dissolved components, however, will usually be sterilized after 30 minutes of 120 degrees celsius. As discussed previously, however, autoclaving of media is prohibitive in terms of equipment, supervisory labor costs, time, and limitations on the complexity and amounts of the media. To obviate the need for this expensive equipment, the preferred embodiment of the present invention utilizes filter sterilization.

When a sterile containment system reaches the user's site, the containment system is placed in barrel 49 of appropriate dimensions. Preferably, the bottom of the storage bag 10 is centered in the bottom of barrel 49. Next, mixing chamber 14 is filled approximately ⅔ full with water for injection through introduction aperture 17 of introduction plate 18.

Powdered cell culture media is next added to mixing chamber 14 through access port 20. Preferably, access port 20 is a two-inch inside threaded flange and plug that opens into mixing chamber 14.

The components of access port 20 are preferably constructed of high-density polyethylene. A constituent container, such as constituent container 26 or any other known container capable of holding a powdered cell culture media is inserted through access port 20 and the contents or a portion of the contents are introduced into the liquid in mixing chamber 14. Pump 24 is next activated and air is withdrawn from the head space of mixing chamber 14 through tube 52. A valve 54 is oriented to allow air drawn from mixing chamber 14 to pass through tube 56 and pump 24, to tube 58. Tube 58 is attached to pump 24 over a barbed tubing connector and is likewise attached to introduction plate 18 over barbed tubing connector 46. An agitation tube 60 is attached to the barbed tubing connector 46 depending downwardly corresponding to the same barbed tubing connector 46 to which tube 58 is attached.

Thus, air extracted from the head space of mixing chamber 14 is passed through the pump and is reintroduced into the bottom of mixing chamber 14 through agitation tube 60. The purpose of the recirculation of this air is to provide a quantity of rising air bubbles which serve to agitate the liquid and powdered constituents of the cell culture media thereby mixing the constituents together. Cap 50 is sealed back over access port 20, and the remainder of the required liquid constituents are added to mixing chamber 14 through tube 62. The liquid cell culture media is next tested and is adjusted for proper pH and osmolarity. Any remaining powdered constituents should be added through access port 20 prior to final mixing of the constituents.

After reconstitution of the powdered cell culture media into liquid form, the media is next sterilized. Although mixing bag 12 and storage bag 10 are both in a sterile condition when received at the reconstitution site, the sterility will have been compromised by opening access port 20 and introducing powdered constituents in mixing chamber 14 even though those powdered constituents may themselves be sterile.

To sterilize the reconstituted media, valve 54 is switched to a position allowing communication between tube 56 and a tube 64. The pump will then need to be reversed or the tubing connected to it in such a manner that fluid may be withdrawn through agitation tube 60 and pumped through tubes 56 and 64 into filter 40. In the embodiment illustrated in FIG. 4, the filter is a sterilizing grade 0.2 micron pore size filter. Filters having pore sizes down to 0.04 microns may also be used in settings requiring ultrafiltration.

Figure 4:
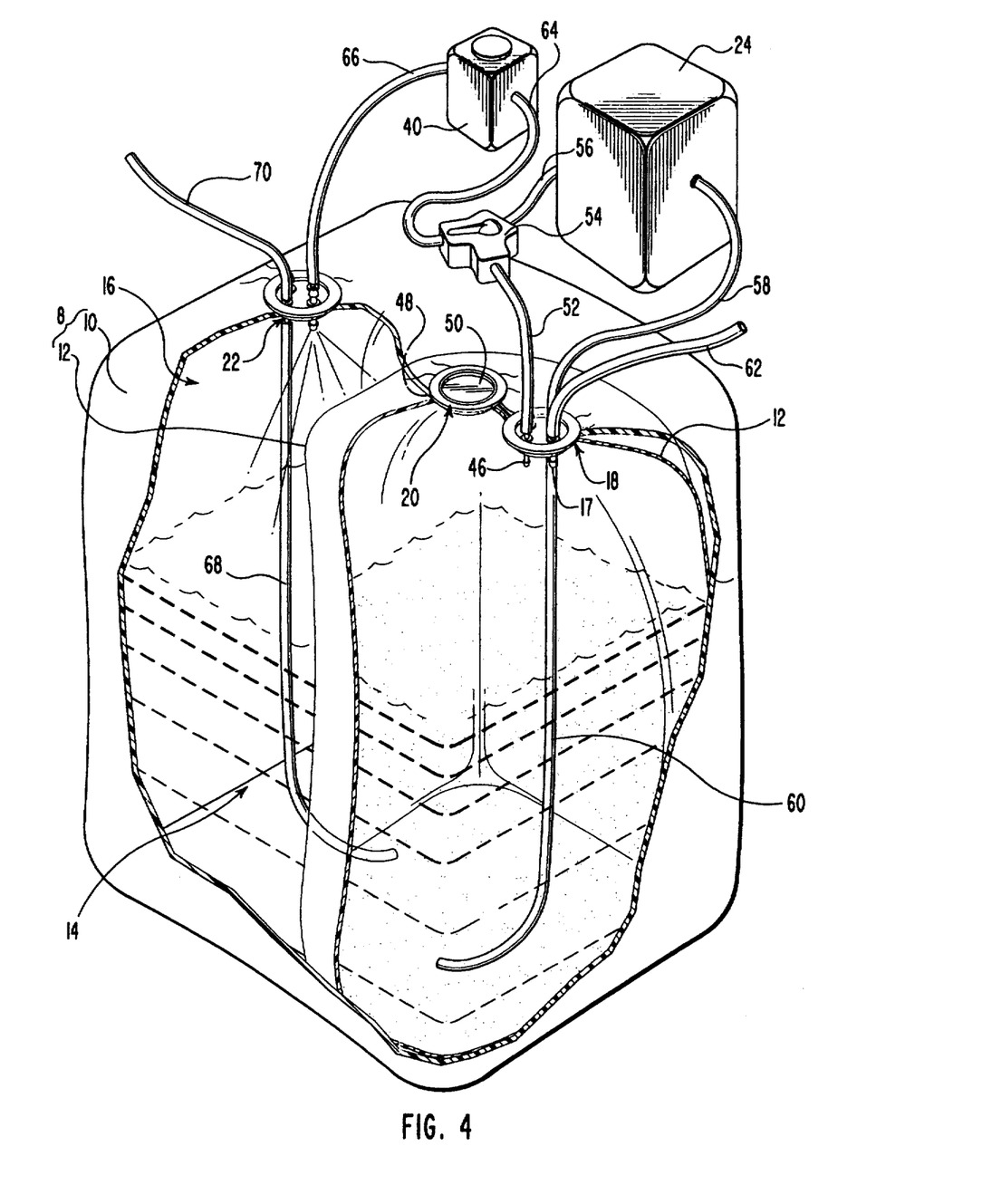
FIG. 4 is a perspective view of the preferred embodiment of the present invention illustrated in FIGS. 1 and 3, illustrating the conveyance of the reconstituted cell culture media from the mixing bag to the storage bag.

After passing though filter 40, the media will be in a sterile condition and will be introduced into sterile storage chamber 16 through tube 66. Tube 66 is attached to dispensing plate 22. The sterile liquid media is conveyed through barbed tubing connector 46 through aperture 17 formed in dispensing plate 22 and enters into the bottom of storage chamber 16.

As liquid media is withdrawn from mixing chamber 14 and is introduced into storage chamber 16, the relative sizes of the bags will begin to change. When liquid is first introduced into mixing chamber 14, mixing bag 12 assumes the size and shape of the barrel within which it is placed. Thus, very little pressure is exerted on the seams located on the top and bottom of the bag as most of the pressure is borne by the sides of the barrel. When fluid is pumped from mixing bag 12 into storage bag 10, storage bag 10 likewise assumes the shape and size of the supporting barrel while mixing bag 12 is reduced in size relative to storage bag 10.

Thus, although the overall size of containment system 8 remains the same, the relative sizes of storage bag 10 and mixing bag 12 change during the conveyance of the liquid media between mixing chamber 14 and storage chamber 16. As the pressure from the liquid outside of mixing bag 12 is substantially equivalent to the pressure on the inside of mixing bag 12 during liquid media convey, there is almost no pressure on the seams of mixing bag 12. As indicated by the dotted lines, the liquid levels between the two bags remain approximately the same throughout the conveyance process.

Figure 5:
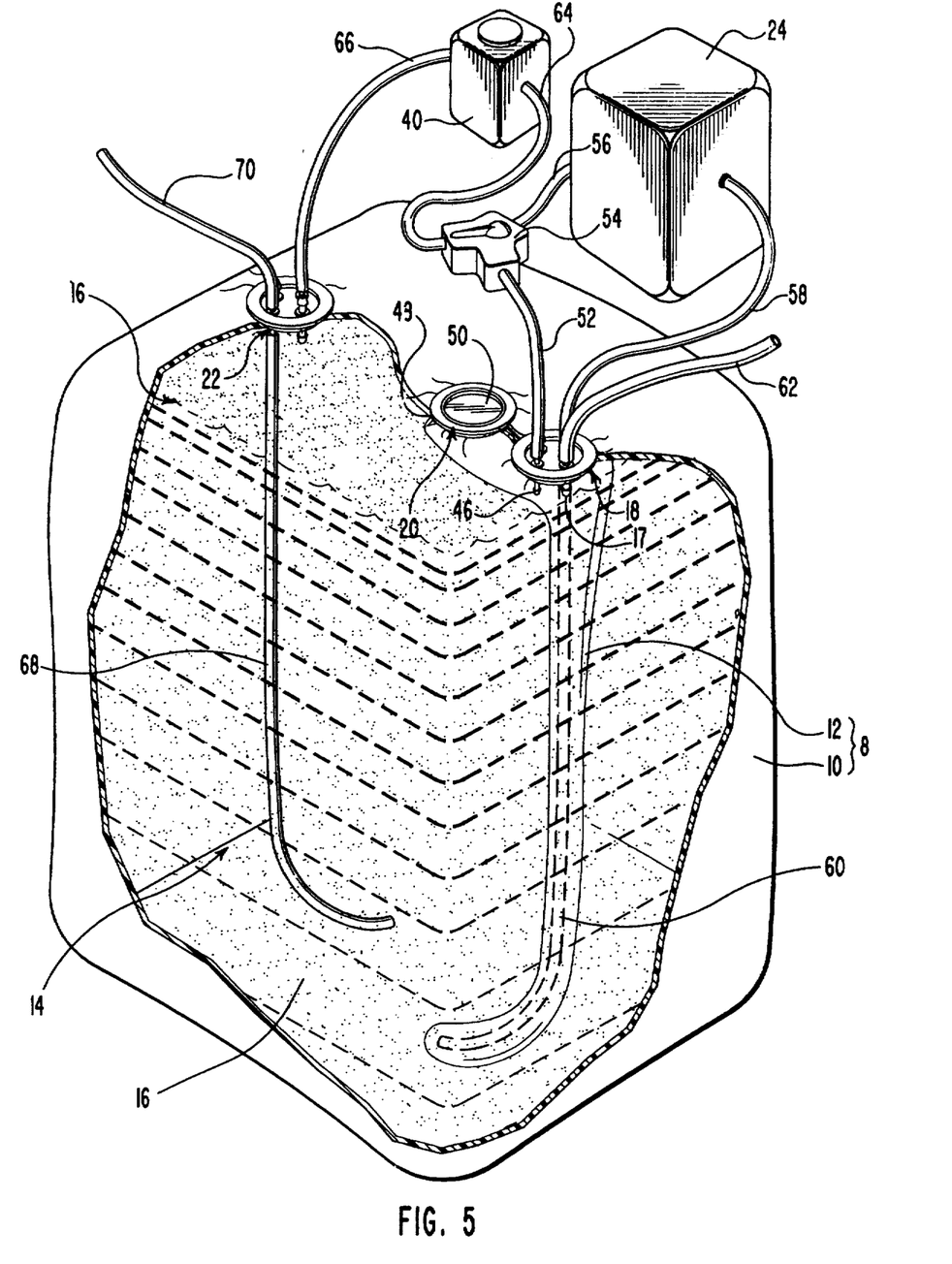
FIG. 5 is a perspective view of the preferred embodiment of the present invention as illustrated in FIGS. 1, 3 and 4 illustrating the relative sizes of the mixing bag and the storage bag when the reconstituted media is being stored ready for dispensing from the storage bag.

When most of the liquid media is conveyed from mixing chamber 14 to storage chamber 16, the relative sizes of storage bag 10 and mixing bag 12 are best illustrated in FIG. 5. Mixing bag 12 has been substantially emptied of its liquid and storage bag 10 is now filled with liquid media in a state ready for storage or dispensing.

If additives are to be introduced into the storage chamber, the mixing technique used to incorporate that additive must be aseptic. One such aseptic mixing system compatible with the embodiment illustrated in FIG. 4 involves pumping sterile air from the headspace of the storage chamber through a series of tubes back into the bottom of the storage chamber. As the sterile air forms bubbles and they rise through the liquid media, agitation of the media occurs thereby incorporating any additives aseptically introduced into the storage chamber through dispensing plate 22.

The present invention is provided with a means for dispensing reconstituted cell culture media from the mixing chamber to the storage chamber. By way of example and not limitation, the dispensing means of the embodiment illustrated in FIG. 4 comprise withdrawal tube 68, dispensing plate 22, and discharge tube 70.

When the liquid media is desired for use, the liquid media is withdrawn from storage chamber 16 through withdrawal tube 68 and out through discharge tube 70. Discharge tube 70 is preferably of a size as to be easily accepted by the cell growth container into which the liquid media is introduced. Likewise, the barbed tubing connector on dispensing plate 22 will be appropriately configured so as to accept discharge tube 70 of the required size. Because of the plurality of apertures 17 formed within dispensing plate 22, a wide variety of barbed tubing connectors may be utilized to provide more versatility of use. Any barbed tubing connector not used, will remain capped and thereby retain the sterility of storage chamber 16.

When all of the liquid media has been dispensed into one or more cell growth containers, containment system 8 may be discarded. As no liquid component has come in contact with the supporting barrel, the supporting barrel may be reused by simply placing a new containment system therein. Since containment system 8 is self-contained, no spillage will occur and, therefore, no clean-up is necessary after use.

As discussed previously, the present invention also contemplates containment systems having a plurality of storage bags and mixing bags. In the embodiment illustrated in FIG. 6, a containment system is depicted which has two storage bags and one mixing bag. This embodiment is constructed substantially similar to the embodiment illustrated in FIG. 1 except that access port 20 and introduction plate 18 must pass through three bag thicknesses to gain access to mixing chamber 14. Access to an intermediate storage chamber 72 is provided through an intermediate dispensing plate 74. Intermediate storage chamber 72 may function as a harvesting bag.

Figure 6:
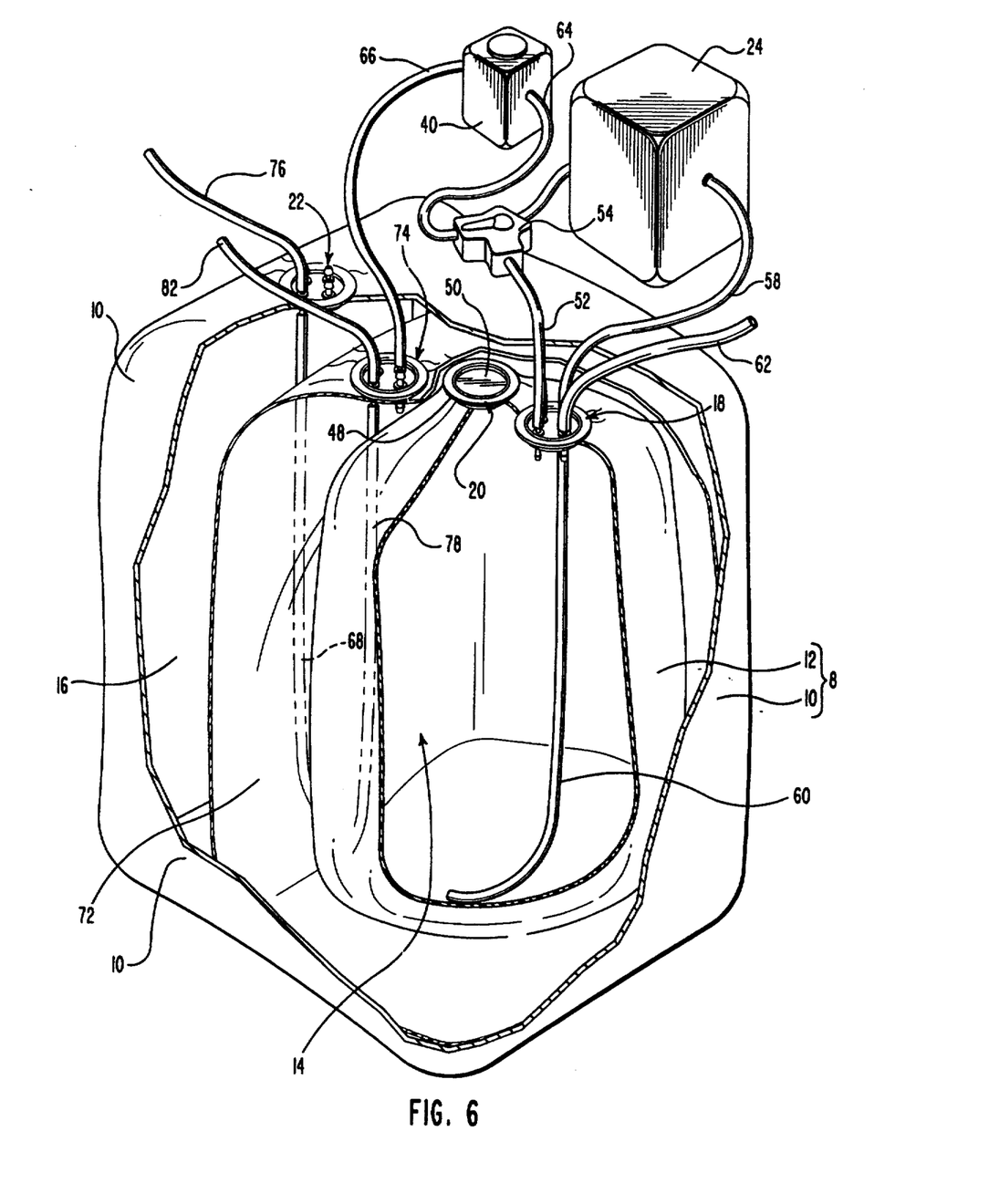
FIG. 6 is a perspective view of an embodiment of the present invention having a first storage bag substantially surrounding the mixing bag and a second storage bag substantially surrounding both the first storage bag and the mixing bag.

The embodiment of FIG. 6 could be utilized when it is desired to harvest media from a cell growth container concomitant with the dispensing of reconstituted liquid cell culture media into the same or another cell growth container. For example, liquid media from a cell growth container ready for harvesting can be withdrawn from the cell growth container into storage chamber 10 through a means for harvesting cell culture media from a cell growth container. By way of example and not limitation, the means for harvesting in the embodiment illustrated in FIG. 6 comprises a retrieval tube 76. Harvested media would pass through retrieval tube 76 to withdrawal tube 68 and be stored in storage chamber 16. Liquid cell culture media stored in intermediate storage chamber 72 can be withdrawn through a diptube 78 and can be discharged through intermediate discharge tube 82 into a cell growth container.

Unlike bags of the prior art, the seams of the bag used in the instant containment system are never exposed to any substantial stress. The powdered cell culture media does not stress the seams of the bags during shipping and the powdered cell culture media is reconstituted within a supporting barrel. As there are no side seams on the inventive bag, the entire bag equally shares the lateral pressure exerted by the liquid media.

As all constituents of the media are mixed inside of the mixing chamber, there is little likelihood of spillage and, as almost no portion of the constituents is lost in the process, fewer adjustments to the final product are necessitated.

In addition, only one barrel need be used for both mixing and storage and simultaneous dispensing and recovery can be conducted. The present invention encompasses bags having a plurality of mixing chambers and storage chambers arranged in the bag within a bag configuration.

While embodiments have been discussed which require the introduction of powdered cell culture media, it will be appreciated that the inventive bag is equally well-suited for the storage, dispensing and harvesting of liquid media. In addition, powdered cell culture media and other powdered constituents could be added to the mixing chamber prior to thermally sealing the mixing chamber thereby obviating the need for an access port.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Patent is:

1. A containment system for use with cell culture media, the containment system comprising:
    a) a mixing bag having a mixing chamber formed therein;
    b) a storage bag having a storage chamber formed therein, the storage bag substantially enclosing the mixing bag;
    c) means for introducing cell culture media constituents into the mixing chamber;
    d) means for conveying liquid cell culture media from the mixing chamber to the storage chamber; and
    e) means for dispensing liquid cell culture media from the storage chamber.

2. A containment system as recited in claim 1, wherein the means for conveying cell culture media further comprises means for sterilizing the cell culture media.

3. A containment system as recited in claim 2, wherein the means for sterilizing comprises a filtration system.

4. A containment system as recited in claim 3, wherein the filtration system comprises a sterilizing grade 0.2 micron pore size filter.

5. A containment system as recited in claim 1, wherein the means for conveying comprises a pump and attendant tubing.

6. A containment system as recited in claim 5, wherein the pump is a peristaltic pump.

7. A containment system as recited in claim 1, wherein the means for conveying further comprises tubing segments connected at each end to barbed tubing connectors connected to and capable of providing fluid communication between the mixing chamber and the storage chamber.

8. A containment system as recited in claim 1, further comprising an access port formed in the mixing bag through which constituents may be introduced into the mixing chamber.

9. A containment system as recited in claim 1, where in the means for introducing comprises a introduction plate through which apertures are formed, wherein the introduction plate is connected to the mixing chamber and is capable of providing fluid communication through the apertures between the mixing chamber and the environment outside of the storage bag.

10. A containment system as recited in claim 9, wherein the means for introducing further comprise a tube dependent from the introduction plate into the mixing chamber.

11. A containment system as recited in claim 1, wherein the means for introducing comprise a powdered cell culture media reservoir connected to and capable of being placed in communication with the mixing chamber.

12. A containment system as recited in claim 10 wherein the means for dispensing comprises a dispensing plate through which apertures are formed, wherein the dispensing plate is connected to the storage chamber and is capable of providing fluid communication through the apertures between the storage chamber and the environment outside of the chamber.

13. A containment system as recited in claim 11, wherein the means for dispensing further comprises tubing attached to barbed tubing connectors affixed in the dispensing plate, said tubing extending both inwardly from the dispensing plate into the storage chamber and outwardly from the dispensing plate.

14. A containment system for use in shipping, and dispensing cell culture media, the containment system comprising:
   a) a mixing bag having a mixing chamber formed therein;
   b) a storage bag having a storage chamber formed therein, the mixing bag residing substantially within the storage bag; and
   c) means for conveying cell culture media from the mixing bag to the storage bag; and
   d) means for dispensing cell culture media from the mixing chamber.

15. A method for reconstituting powdered cell culture media within a containment system, the method comprising the steps of:
   a) introducing the powdered and liquid constituents of cell culture media into a mixing chamber of a mixing bag substantially enclosed by a storage bag;
   b) mixing to reconstitute the constituents in the mixing chamber; and
   c) conveying the reconstituted cell culture media from the mixing chamber to the storage chamber.

16. A method for reconstituting powdered cell culture media as recited in claim 15, wherein the method further comprises the step of sterilizing the reconstituted cell culture media.

17. A method for reconstituting powdered cell culture media as recited in claim 15, wherein the method further comprises the step of sterilizing the mixing chamber and the storage chamber prior to the introduction of the constituents of a powdered cell culture media.

18. A containment system for use with cell culture media, the containment system comprising:
   a) a mixing bag having a mixing chamber formed therein;
   b) an intermediate storage bag having an intermediate storage chamber formed therein, the intermediate storage bag substantially enclosing the mixing bag;
   c) a storage bag having a storage chamber formed therein, the storage bag substantially enclosing the intermediate storage bag;
   d) means for conveying liquid cell culture media from the mixing chamber to the intermediate storage chamber;
   e) means for dispensing liquid cell culture media from the intermediate storage chambers; and
   f) means for harvesting cell culture media into the storage bag from a cell growth container.

19. A containment system for use with cell culture media, the containment system comprising:
   a) a mixing bag having a top and a bottom and having a mixing chamber formed therein;
   b) a storage bag having a top and a bottom and having a storage chamber formed therein, the storage chamber substantially enclosing the mixing bag;
   c) a dispensing plate affixed through the top of the storage bag, the dispensing plate having an aperture formed therethrough capable of communicating between the storage chamber and the environment outside of the storage bag;
   d) an introducing plate affixed through the tops of both the mixing bag and the storage bag capable of communicating between the mixing chamber and the environment outside of the storage bag; and
   e) a pump and tubing communicating between the mixing chamber and the storage chamber.

* * * * *

UNITED STATES PATENT AND TRADEMARK OFFICE
CERTIFICATE OF CORRECTION

PATENT NO. : 5,362,642
DATED : November 8, 1994
INVENTOR(S) : Dale G. Hern

It is certified that error appears in the above-indentified patent and that said Letters Patent is hereby corrected as shown below:

Title page, abstract, column 2, line 11, "maybe" should be --may be--.

Column 6, line 54, "reinforce" should be --reinforced--.

Column 8, line 3, delete "a".

Column 8, line 66, delete "an".

Column 9, line 62, after "of" insert --the--.

Column 12, line 43, "convey" should be --conveyance--.

Column 14, line 65, "a introduction" should be --an introduction--.

Column 14, lines 64-65, "where in" should be --wherein--.

Column 15, line 32, delete "and".

Signed and Sealed this

Sixteenth Day of May, 1995

*Attest:*

BRUCE LEHMAN

*Attesting Officer*    Commissioner of Patents and Trademarks